US006770278B1

(12) United States Patent
Skelly

(10) Patent No.: US 6,770,278 B1
(45) Date of Patent: Aug. 3, 2004

(54) METHODS OF MAKING AND USING IMMUNOGLOBULIN (IG) COMPOSITIONS

(75) Inventor: William G. Skelly, Kansas City, MO (US)

(73) Assignee: Central Biomedia, Inc., Lenexa, KS (US)

( * ) Notice: Subject to any disclaimer, the term of this patent is extended or adjusted under 35 U.S.C. 154(b) by 0 days.

(21) Appl. No.: 09/586,510

(22) Filed: Jun. 2, 2000

Related U.S. Application Data

(63) Continuation of application No. 08/685,052, filed on Jul. 23, 1996, now abandoned, which is a continuation-in-part of application No. 08/349,010, filed on Dec. 2, 1994, now Pat. No. 5,548,066.

(51) Int. Cl.$^7$ ...................... A61K 39/395; C07K 16/00; C07K 16/77

(52) U.S. Cl. ............................... 424/130.1; 424/157.1; 424/530; 424/531; 424/524; 530/387.1; 530/389.1; 530/829; 530/830; 530/831

(58) Field of Search ........................... 424/130.1, 157.1, 424/530, 531, 529; 530/387.1, 389.1, 829, 830, 831

(56) References Cited

U.S. PATENT DOCUMENTS

| 2,386,725 | A | 10/1945 | Strean |
| 3,704,089 | A | 11/1972 | Stehlik |
| 3,743,480 | A | 7/1973 | Falk |
| 4,349,539 | A | 9/1982 | Wampler |
| 4,620,908 | A | 11/1986 | Van Duzer |
| 4,663,058 | A | 5/1987 | Wells et al. |
| 4,665,159 | A | 5/1987 | Dobkin |
| 5,362,442 | A | 11/1994 | Kent |

OTHER PUBLICATIONS

Hillidge et al., J. Equine Vet. Sci., 6:302–304, abstract from Dialog, CAB 01835289, CAB Acc. No. 872292919.*
W.L. Ragland, DVM, PhD, et al., "Passive Immunotherapy of Equine Respiratory Disease: Treatment of Acutely Ill Horses With Equine Immunoglobulin," The Equine Athlete, Nov./Dec. 1995, vol. 8, No. 6, 1–6.
Steven B. Constant, DVM, et al., "Serum immunoglobulin G concentration in goat kids fed colostrum or a colostrum substitute," JAVMA, Dec. 15, 1994, vol. 205, No. 12, pp. 1759–1762.
John E. Van Wye, M.D., et al., "Pseudomonas Hyperimmune Globulin Passive Immunotherapy for Pulmonary Exacerbations in Cystic Fibrosis," Pediatric Pulmonology, (1990), vol. 9, pp. 7–18.
Alan Johnstone, et al., "Immunochemistry in Practice," Blackwell Sci. Pub., 1987, pp. 33–34.

Beverly L. Mangold and David A. Dean, "Passive Transfer with Serum and IgG Antibodies of Irradiated Cercaria–Induced Resistance Against Schistosoma Mansoni in Mice," The Journal of Immunology, Apr. 1, 1986, vol. 136, No. 7, pp. 2644–2648.
Masayuki Iwata, et al., "Antipyretic activity of human immunoglobulin preparations for intravenous use in an experimental model of fever in rabbits," Clinical Use of Intravenous Immunoglobulins, 1986, pp. 327–338 , Academic Press Inc. (London) Ltd.
Val G. Hemming, et al., "Immunoglobulins in respiratory syncytial virus infections," Clinical Use of Intravenous Immunoglobulins, 1986, pp. 285–294, Academic Press Inc. (London) Ltd.
T. Nishimura and R. Fujil, "Therapeutic evaluation of combination therapy with immunoglobulin (IG–100) and antibiotics against severe paediatric infections," Clinical Use of Intravenous Immunoglobulins, 1986, pp. 367–372, Academic Press Inc. (London) Ltd.
K. Matsumoto, et al., "Therapeutic evaluation of combination therapy with Immunoglobulin (IG–100) and antiobiotics against sever infections," Clinical Use of Intravenous Immunoglobulins, 1986, pp. 363–366, Academic Press Inc. (London) Ltd.
Matthew Pollack, "Antibody therapy in Gram–negative bacterial disease," Clinical Use of Intravenous Immunoglobulins, 1986, pp. 317–326, Academic Press Inc. (London) Ltd.
Michael P. Glauser and J.D. Baumgartner,"Septicaemia and shock in Gram–negative bacterial infections," Clinical Use of Intravenous Immunoglobulins, 1986, pp. 355–362, Academic Press Inc. (London) Ltd.
J. Bussell, et al., "Prophylaxis of neonatal sepsis with intravenous gammaglobulin," Clinical Use of Intravenous Immunoglobulins, 1986, pp. 171–175, Academic Press Inc. (London) Ltd.
Victor S. Blanchette, et al., "Role of Intravenous Immunoglobulin G in Autoimmune Hematologic Disorders," Seminars in Hematology, Jul. 1992, vol. 29 No. 3, Suppl. 2, pp. 72–82.

(List continued on next page.)

Primary Examiner—Ronald B. Schwadron
(74) Attorney, Agent, or Firm—Stinson Morrison Hecker LLP

(57) ABSTRACT

The invention is directed to methods of using Ig compositions to prevent and/or treat humans, livestock and/or domesticated animals suffering from stress induced respiratory disorders. The Ig composition comprises a concentrated amount of one or more immunoglobulins selected from the group consisting of alpha, beta, and gamma globulins. Preferably, the Ig composition comprises other antibodies identified as providing an immune response and/or immune factors such as complement and transfer factors. The Ig composition preferably includes immunoglobulins specific to a variety of antigens. In a preferred method, an equine Ig composition is used to treat exercise induced pulmonary hemorrhage in horses.

14 Claims, No Drawings

OTHER PUBLICATIONS

Howard H. Erickson and M. Roger Fedde, "What Causes Racehorse Lungs to Bleed," The Quarter Racing Journal, May 1995, pp. 52–57.

Glenn Flores, et al., "Efficacy of Intravenous Immunoglobulin in the Treatment of Autoimmune Hemolytic Anemia: Results in 73 Patients," American Journal of Hematology, 1993, vol. 44, pp. 237–242.

Gittan Gröndahl, et al., "Opsonic effect of equine plasma from different donors," Veterinary Microbiology, 1997, vol. 56, pp. 227–235.

Arnold I. Levinson, MD and Lisa M. Wheatley, MD, "Intravenous immunoglobulin: A new therapeutic approach in steroid–dependent asthma?," Journal of Allergy and Clinical Immunology, Oct. 1991, vol. 88, No. 4, pp. 552–554.

B. Baker, et al, "Endotaxaemia in Racehorses Following Exertion," Journal of the South African Veterinary Association, Jun. 1988, pp. 63–66.

H. Erickson, "Exercise Induced Pulmonary Haemorrhage," Equine Veterinary Journal Supplement 1995, vol. 18, pp. 476–478.

* cited by examiner

METHODS OF MAKING AND USING IMMUNOGLOBULIN (IG) COMPOSITIONS

This application is a Continuation of U.S. patent application Ser. No. 08/685,052, filed Jul. 23, 1996, now abandoned, which is a Continuation-in-Part of U.S. patent application Ser. No. 08/349,010, filed Dec. 2, 1994, which is now issued as U.S. Pat. No. 5,548,066, both of which are hereby incorporated herein by reference.

BACKGROUND OF THE INVENTION

1. Field of the Invention

The present invention is generally directed to immunoglobulin (Ig) compositions and methods of therapeutically using Ig compositions in animals including humans, livestock and domesticated animals. Several embodiments of the invention are directed to unique and novel methods of using Ig compositions in the treatment of certain maladies or conditions. These methods include the use of an Ig composition for treating stress induced respiratory disorders, diarrhea such as diarrhea caused by Parvovirus in canines, and epithelial tissue disorders including non-specific skin lesions, lymphoid hyperplasia and guttural pouch infections. Another embodiment of the invention is directed to a method for using Ig compositions to enhance weight gain in livestock. Yet a further embodiment is directed to new techniques for administering Ig compositions which are more convenient and/or more effective for a particular purpose.

The present invention is also directed to an improved Ig composition and method of making the same. The inventive composition is a sterile plasma product comprising a wide range of immunoglobulins (antibodies), and other immune constituents obtained from whole blood including complement and transfer factors extracted from white blood cells. This improved composition may be used in the novel methods of treatment described above, as well as for other applications known in the art including for use in providing passive immunity, treating auto-immune diseases, and treating various bacterial, fungal, and viral infections.

2. Description of the Related Art

It is known in the art that passive immunity may be imparted to an immune deficient patient by administering to the patient immunoglobulins (Ig) and other immune factors obtained from a donor having known immunity. For example, mother's milk includes a composition known as colostrum which provides the newborn with immunoglobulins and other immune factors to protect it from disease until the newborn's own immune system is more fully developed. Drawing from nature's example, filtered plasma or serum derived from collected whole blood and containing immune factors has been utilized to convey passive immunity to patients suffering from hypogammaglobulinemia or failure of passive transfer. Intravenous (IV) or intramuscular (IM) therapy has also been used either alone or in combination with antibiotics for treating specific bacterial, fungal or viral infections, and reportedly has therapeutic effects in patients having autoimmune diseases. Thus Ig containing serums have been administered intramuscularly and intravenously for treating patients who are classified as "immune challenged" in some manner. While these prior methods of treatment and administration are of great importance in the field, there remains a need to improve upon the quality and effectiveness of these methods and to expand upon the types of applications for which Ig compositions may be used. In addition, there is a need to improve upon the methods of administration so as to enhance the convenience and effectiveness of the compositions.

A particularly useful Ig composition and method of making the same was disclosed by the present inventor in U.S. Ser. No. 08/349,010 filed Dec. 2, 1994, and issuing as U.S. Pat. No. 5,548,066, which is fully incorporated herein by reference (the "'010 method"). In the '010 method, the immunoglobulin composition is prepared from whole blood collected from donors having known immunity to one or more antigens. The drawn blood is allowed to clot such that the cellular material and clotting factors (erythrocytes, lymphocytes, platelets, fibrin, etc.) are separated from the serum portion of the blood. During this clotting process some of the white blood cells rupture such that "transfer factors" and other constituents of the white blood cells spill into the serum. The serum is then separated from the clotted cells and filtered to remove all of the cellular fragments, thereby producing a serum product. This filtered serum product may then be concentrated via removal of water and other low molecular weight substances. The concentrated serum is then sterilized, but not denatured, by a novel method of freezing the serum and subjecting it to specified doses of gamma irradiation while frozen. Once sterilized, the serum can be thawed and stored as a liquid under refrigeration conditions for several months.

The resulting composition of the '010 method comprises a sterile and concentrated serum having a wide range of immunoglobulins or antibodies and other immune constituents such as the "transfer factors" expressed from the white blood cells. The '010 preparation is particularly useful for immunotherapy insofar as the serum is readily available to the user in a convenient purified and liquid refrigerated form. In the past, commercial plasma used for immunotherapy (particularly by ranchers in treating livestock) was required to be kept frozen requiring the user to thaw and filter the plasma just before use. The '010 composition in contrast is immediately ready for use. The '010 composition is also advantageous in that it can be used for oral administration, in addition to conventional intravenous injection. Oral administration is preferred in certain circumstances because the immunoglobulins may be more readily absorbed and distributed within the patient. Furthermore, oral administration is more convenient and safer than intravenous applications which require careful control and monitoring of drip rate.

While the '010 composition has many advantages over compositions of the prior art, the technique of clotting the blood to separate the cellular and serum fractions has some drawbacks. In particular, insofar as complement in the blood is thermolabile, a certain amount of complement may be degraded ova time while the blood is allowed to clot. Furthermore, it is believed that white blood cells may become trapped within the red blood cells during the clotting process such that a portion of these cells remain intact and do not expel transfer factors into the serum. For this reason, the total amount of complement and transfer factors available in the collected blood is not expressed in the final product.

It is therefore an object of the present invention to provide new methods of using and administering immunoglobulin compositions for therapeutic and/or livestock management purposes.

Another object of the invention is to provide an improved immunoglobulin composition and method of making the same.

SUMMARY OF THE INVENTION

These and other objects are achieved by several methods discovered by the inventor of using immunoglobulin (Ig) preparations for therapeutic and/or livestock management purposes.

Of particular import, the inventor has discovered a novel method of enhancing weight gain in patients, particularly cattle and other livestock, wherein the method comprises administering one or more doses of an immunoglobulin composition to the animal. In this method, the Ig composition may be administered in any conventional manner or is preferably administered via a novel method of subcutaneous injection which is particularly convenient and effective for this purpose.

The inventor has also discovered a method of preventing and/or treating stress induced respiratory disorders including bovine and porcine respiratory disease complex, upper respiratory infections in horses and exercise induced pulmonary hemorrhage. In this method, one or more doses of an immunoglobulin composition is administered to the animal preferably immediately before or after the stressful occurrence. While any conventional mode of administration is deemed suitable, the inventor has found that for purposes of treating livestock such as cattle, the novel method of subcutaneous injection is preferred. For purposes of treating horses, direct application to the lungs via intratracheal injection or vapor inhalation is preferred.

Yet another method developed by the inventor is a novel method of treating diarrhea including diarrhea caused by Parvovirus in canines. This method comprises administering an immunoglobulin composition to the patient in any conventional manner with oral and/or subcutaneous administration being most preferred.

The inventor has also discovered methods for treating epithelial tissue disorders such as non-specific skin lesions, lymphoid hyperplasia and guttural pouch infections. This method comprises administering one or more doses of an Ig preparation to the patient suffering from the disorder. In these methods, the Ig preparation may be administered in any conventional manner but is particularly useful if administered via novel modes of subcutaneous injection or direct application to the affected tissue.

In another embodiment of the invention, the inventor has developed an improved Ig composition and method of making the same whereby the composition is prepared from whole blood without permitting the blood to clot before extraction. It is believed that this improved method increases the overall amount of immunoglobulins, complement, transfer factors and other immune constituents extracted from the whole blood. The improved method includes the steps of collecting whole blood from one or more donors, wherein the donors have known immunity for a variety of ailments. An anti-coagulant such as citrate-phosphate-dextrose (CPD) is then mixed with the collected blood in sufficient amount to prevent the blood from clotting. The anti-coagulant and whole blood mixture is then allowed to stand undisturbed until the red blood cells contained within the blood settle to the bottom of the collection vessel forming a bottom red blood cell layer. The white blood cells and liquid plasma form middle and upper layers respectively. In some species, it may be necessary to subject the anti-coagulant and whole blood mixture to centrifugation in order to obtain this layered separation.

Upon separation, the plasma and white blood cell layers are immediately separated from the red blood cell layer and preferably chilled. The white blood cells and plasma are then subjected to one or more filtration steps whereby at least a portion of the white blood cells are ruptured so that transfer factors contained within the white blood cells spill into the liquid plasma. The cellular fragments do not pass through the filter such that the resulting filtered plasma substantially comprises a liquid. Optionally, the filtered plasma may be concentrated to remove water and other low molecular weight components. The filtered and/or concentrated plasma is then sterilized preferably by freezing the plasma and irradiating the plasma while in the frozen state. The sterilized plasma may then be allowed to thaw and to be stored in a liquid state under refrigerated conditions.

DETAILED DESCRIPTION OF THE INVENTION

Part A—Novel Methods of Using Immunoglobulin Compositions

In several embodiments of the invention, novel methods of using and administering immunoglobulin (Ig) compositions are disclosed. For purposes of each of these inventive methods, any Ig composition as hereafter defined meeting known standards of sterility and recipient compatibility shall be considered suitable. The term "Ig composition" shall mean any composition comprising a concentrated amount of one or more immunoglobulins selected from the group of alpha, beta and gamma globulins and/or comprising other antibodies identified as providing an immune response. The Ig composition preferably comprises a concentrated amount of one or more gamma globulins selected from the group consisting of IgG, $IgG_T$, IgM, IgA, IgE and/or IgD, and most preferably includes IgG immunoglobulins specific to a variety of different antigens.

The concentration level of the composition can be assessed with reference to the IgG concentration insofar as IgG levels are generally considered a good indicator of overall Ig levels. For purposes of each of the methods of the present invention, the Ig composition will generally include IgG in amounts ranging from 20–200 mg/ml of the composition, preferably 30–100 mg/ml and most preferably 40–80 mg/ml of the composition. The IgG levels can be readily determined by radial immunodiffusion as is known in the art.

The Ig composition to be used for each method of the present invention will preferably reflect a wide range of immunoglobulins and other immune factors. This means that in addition to the immunoglobulins or antibodies referenced above, the Ig composition will similarly include an amount of complement which is known to assist antibodies in the immune response, and may also include transfer factors obtained from the internal fluid of white blood cells. The Ig composition should be relatively free of red blood cells or any red blood cell constituents such as hemoglobin to avoid adverse effects in the recipient.

Particularly useful Ig compositions for purposes of the present invention are selected from the group consisting of Ig compositions made in accordance with U.S. patent application Ser. No. 08/349,010 incorporated herein by reference (the "010 method"), and/or made in accordance with the improved method of preparing Ig compositions hereafter disclosed in Part B of the present application (the "inventive method of the present invention").

Enhance Weight Gain in Livestock and Subcutaneous Injection

The inventor has discovered a new method of enhancing weight gain in livestock particularly in young calves, wherein the method comprises administering one or more doses of an Ig composition to the animal. While the inventor does not wish to be limited by speculation as to the cause of this increased weight gain, it is believed that the Ig composition may contribute to weight gain by blocking the activity of interleukin which often negatively impacts appetite.

In a preferred embodiment, a single dose of the Ig composition will be administered to each calf. The dosage amount of the Ig composition will vary depending upon the size of the animal and concentration of the Ig composition. In general, it is contemplated that a single dose of the Ig composition will range from 2 to 10 ml/100 pounds (lbs) of the animal.

The Ig composition may be administered to the animal orally, intravenously or by other conventional means now known or later developed in the art. In a preferred embodiment, the inventor has discovered that the Ig composition can be administered by subcutaneous injection, preferably in the area of the neck, with good results. This method of administration is deemed particularly useful for treating livestock, insofar as the injection can be conveniently and easily administered without unduly restraining the animals.

This novel method of administering Ig compositions via subcutaneous injection may also be used for other applications such as in conventional Ig treatment of bacterial, fungal and/or viral infections. In the past, these infections were treated with Ig compositions via intravenous or intramuscular injections. These types of injections, however, are relatively difficult to perform on large herds of animals. It has been found that subcutaneous injection either alone or in combination with antibiotic therapy is well adapted for use in treating these infections, and in view of the ease of administration is much more convenient and effective.

Stress Induced Respiratory Disorders

In one embodiment of the invention, the inventor has discovered a new method of preventing and/or treating stress induced respiratory disorders which commonly occur in animals such as cattle, pigs and horses. The inventive method comprises administering one or more doses of an Ig composition as described above to the animal. In order to prevent the onset of the disorder, the Ig composition is preferably administered immediately before and/or after the stressful occurrence. In order to treat the disorder, the Ig composition is preferably administered in regular doses until the condition subsides.

This method is useful in preventing and treating bovine and/or porcine respiratory disease complex which often occurs in cattle and swine respectively when shipped or corralled for slaughter. Insofar as antibiotic treatment is not generally recommended for use on animals approaching slaughter, this method of treatment is particularly well suited for treating the complex. It is suggested that each animal be administered a dose of the Ig composition immediately prior to and/or after shipment or relocation. In this manner, the Ig composition acts to fend off or prevent the onset of the complex. The dosage amount will vary depending upon the concentration of the composition, and will generally range from 1 to 10 ml/100 lbs. body weight of the animal.

The Ig composition may be administered to the cattle and/or swine intravenously or by other appropriate means now known or later developed in the art. In a preferred embodiment, the composition will be administered by subcutaneous injection, preferably in the region of the neck. As previously discussed, this novel method of administering an Ig composition is deemed particularly well suited for treating livestock since the animals may be conveniently injected as they are being corralled for shipment.

The present method may also be used for treating upper respiratory infections which often accompany stress in horses such as caused by shipping or transport. In this method, it is suggested that one or more doses of the Ig composition as described above be administered to the horse as clinical conditions indicate until the infection is abated. While the dosage amount will vary depending upon the concentration of the composition and the size of the animal, it is preferable to administer doses in volume amounts ranging from 2 to 20 ml of the composition.

The inventor has discovered that exercise induced pulmonary hemorrhage, a respiratory condition commonly affecting horses that engage in strenuous activity such as racing, may also be successfully treated by administering to the horse one or more doses of an Ig composition as described above. The amount of each dose will vary depending upon the concentration of the composition and size of the animal and will generally range from about 5 to 20 ml of the composition.

If the horse is racing on a regular basis, it is preferable to administer a dose of the Ig composition three to five times within a six to ten day period, as well as immediately prior to racing if permitted by the rules. If the horse to be treated is not entered to race for an extended period of time of more than a week, the preferred method would be to administer a dose of the Ig composition every seven to ten days.

With respect to treating both upper respiratory infections and exercise induced pulmonary hemorrhage in horses, the Ig composition may be administered to the horse orally, intravenously, subcutaneously as described above, or by other means now known or later developed in the art. In a preferred method, the inventor has discovered novel methods of administering the Ig composition directly to the area of the lung tissue via intratracheal injection and/or vapor inhalation.

In the method of intratracheal injection, the Ig composition is supplied via a syringe or fiberoptic scope routed through the trachea into the lung area. By using this method of administration, the Ig composition may be directly applied to one or both of the individual lungs and/or to specific portions of the lung tissue that are infected. It has been found that by concentrating the composition within the area of the infection, as opposed to circulating the composition throughout the animal's body, the treatment is more effective.

Vapor inhalation is a novel method of administration which generally comprises the steps of vaporizing a dose of the Ig composition to be administered and causing the horse or other recipient to inhale the vaporized dose. This method of administration may be accomplished by running the Ig composition through an ultrasonic nebulizer which converts the liquid composition to a vapor. The vapor may then be inhaled by the recipient through a mask or the like. Vapor inhalation, like intratracheal injection, has been found by the inventor to be particularly well suited to treating respiratory or lung-related problems insofar as the composition is directly applied to the area of concern.

Diarrhea and Parvovirus

The inventor has also discovered a new method for treating patients having diarrhea including canines suffering from Parvovirus. This method comprises administering one or more doses of the Ig composition to the patient on a daily basis until clinical conditions subside. The dosage amount will vary depending upon the concentration of the composition and size of the animal and will generally range from 1 to 20 ml of the Ig composition.

The Ig composition may be administered to the patient orally, intravenously, subcutaneously or by other appropriate means now known or later developed, with oral or a combination of oral and subcutaneous application being most preferred. In treating dogs having Parvovirus, for example, it is suggested to orally administer a dose of the Ig composition ranging from 1–2 ml/kg body weight of the animal, along with subcutaneous injection of a fractional dose of Ig composition, preferably ranging from 0.1–0.2 ml/kg body weight of the animal.

Epithelial Tissue Disorders

A further method of the present invention is directed to a method of treating epithelial tissue disorders such as non-specific skin lesions, lymphoid hyperplasia, and guttural pouch infection. In this method, one or more doses of an Ig composition are administered to the animal suffering from the disorder until clinical conditions subside.

It has been found that non-specific skin lesions which often occur in canines, for example, may be effectively treated by the administering one or more doses of an Ig composition to the afflicted dog. While any conventional means of administering the composition now known or later developed in the art is deemed suitable for purposes of treating these lesions, the best mode known for practicing the invention comprises subcutaneously injecting the animal with a dose of an Ig composition ranging from 0.1 to 0.2 ml/kg body weight of the animal.

In another embodiment, the inventor has discovered that animals suffering from lymphoid hyperplasia may be treated by directly applying one or more doses of an Ig composition to the lesions which are caused by the condition. In this embodiment, the Ig composition will be sprayed onto the lesions as a single dose once daily until the clinical conditions improve. The dosage amount will vary depending upon the concentration of the composition and will generally range from 10 to 20 ml of the composition.

Another form of epithelial tissue disorder known as guttural pouch infection occurs in horses and may be treated via this method. In this embodiment, the Ig composition is again applied to the area of infection, namely by infusing the Ig composition directly into the pouch. The Ig composition will preferably be infused once daily in dosage amounts ranging from 1 to 10 ml of the composition until the clinical conditions subside.

Part B—Improved Method of Making an Immunoglobulin Composition

An improved immunoglobulin (Ig) composition may be prepared from the whole blood of one or more donors, preferably from a plurality of donors. It is advantageous that the donors comprise mature members of the species so as to assure that each donor will have been exposed to a number of different antigens during his or her lifetime and will thus have immunity against a wider variety of antigens. The use of a plurality of donors will likewise increase the type and number of different antibodies obtained from the collected blood.

If the Ig composition is to be used in providing passive immunity and/or in treating a specific disease or infection, it is preferable that a majority of the donors have been exposed to that particular disease or condition such that they have immunity respective of that disease. In that regard, it may be desirable in fact to immunize the donor group as against one or more antigens to increase their level of immunity and obtain a more consistent level of immunity within the donor population.

Lastly, in order to obtain a consistent product, it is also preferable that the blood be collected from a relatively large donor group. For example, in the case of preparing equine serum it is preferable to collect the blood from a herd of fifty or more. Furthermore, it is advantageous that the members of this group originate from different geographic regions so as to contribute immunity to pathogens of various regions of the country.

As is more fully explained in U.S. application Ser. No. 08/349,010 which is fully incorporated herein by reference, the group of donors may comprise a live herd that is bled on a regular basis and maintained for the purpose of producing Ig compositions, or may consist of blood collected from slaughtered animals.

The whole blood may be collected from the donors in any manner deemed suitable and known in the art for that particular species of donor. An example of a suitable method of collecting whole blood from livestock is fully described in U.S. Ser. No. 08/349,010 which is incorporated herein by reference. Similar methods are known and adapted for use in collecting blood from other donor species including humans.

In order to prevent the blood from coagulating on the interior of the collection vessel and to prevent the blood from clotting upon collection, an anti-coagulant is added to the collection container into which the blood is collected. The anti-coagulant should be added to the collected blood in an amount sufficient to substantially prevent the blood from clotting. Any anti-coagulant known in the art which prevents blood from clotting and not associated with adverse effects when administered to the intended recipient of the Ig composition is deemed suitable for these purposes.

The anti-coagulant citrate-phosphate-dextrose (CPD) which is commonly used as an anti-coagulant in blood collection operations is deemed particularly suitable for these purposes. Use of the anti-coagulant heparin is discouraged insofar as it is anticipated that the heparin would have a residual adverse effect in the patient upon administration of the final Ig composition.

In accordance with the present invention, the anti-coagulant may be added to the collection container with stirring in a manner to result in a consistent ratio of anti-coagulant to whole blood. The ratio will vary depending upon the type of anti-coagulant and preferably comprises the minimum amount of anti-coagulant necessary in order to prevent the blood from clotting. Where the anti-coagulant comprises CPD, it is suggested that one part of CPD by volume be added to every nine parts of whole blood by volume.

Once the desired amount of whole blood is collected, the mixture of CPD and whole blood is allowed to stand undisturbed until the red blood cells settle to the bottom of the container to form a bottom layer. The white blood cells will form a middle layer immediately above the red blood cell layer, and the liquid plasma portion of the blood forms a top layer. This layered separation of the components can be visually monitored.

In the case of equine blood, this layered separation will occur within a relatively short amount of time less than one hour. In other species of animals, the sedimentation rate may be such that complete layered separation is difficult to achieve within a feasible amount of time to avoid denaturing of the complement. In these instances, it is suggested that the whole blood be subjected to centrifugation in order to expedite the layering process, but in a manner to avoid rupturing the red blood cells.

Once the layers are formed, the upper layers of liquid plasma and white blood cells ("WBC") are removed by any means deemed suitable to obtain a WBC/plasma mixture without the inclusion of red blood cells. Preferably, the white blood cell and plasma layers are removed by suction such as by using a hose under vacuum. The bottom-most portion of the white blood cell layer should not be removed so as to assure that the red blood cells remain undisturbed. Once the WBC/plasma mixture is withdrawn, it is immediately chilled to a temperature of less than 50° F. so as to avoid degradation of any complement contained within the mixture.

The chilled WBC/plasma mixture is then filtered in such a manner as to cause at least a portion of the white blood cells contained within the WBC/plasma mixture to be ruptured. By rupturing the white blood cells, transfer factors within the white blood cells are expressed into the liquid plasma and admitted through the filters. The cellular fragments are removed by the filters so as to result in a filtered liquid plasma product.

This filtration step may be achieved by first pumping the chilled WBC/plasma mixture through a Cuno-type filter thereby rupturing some of the white blood cells and removing the cellular fragments. The plasma may then be passed through a series of filters of progressively smaller pore size beginning with a 0.65 micron filter, then a 0.2 micron nominal filter, and lastly a 0.2 micron absolute filter.

The filtered plasma may optionally be concentrated to reduce the volume of the composition by removing excess water and other low molecular weight substances. Certain recipients, such as infant mammals, cannot accept large quantities of medication intravenously due to a lack of capacity. Therefore, reducing the total volume of the composition to be administered while retaining the amount of protective immunoglobulins and other immune factors is deemed particularly advantageous in compositions intended for infant use.

The concentration step is preferably performed by ultrafiltration to remove water molecules and other low molecular weight substances, as is known in the art using a cut-off filter of size preferably ranging from 10,000 to 100,000 M.W. During the concentration process, samples of the plasma may be taken to determine if the plasma has been sufficiently concentrated. In this regard, the final concentrated plasma is preferably concentrated up to about 6 times the IgG level of the starting filtered plasma and most preferably 1.5 to 4 times the IgG level of the starting filtered plasma. For example, if the starting filtered plasma has an IgG concentration of 1 g/100 ml, then the concentration process may be stopped when later tests report an IgG concentration of between about 1 to 7 g/100 ml, and preferably about 3 g/100 ml. The determination of the IgG amount may be made by the radial immunodiffusion test which is well known in the art. Alternatively, the total immunoglobulin (Ig) concentration can be determined by using serum protein electrophoresis.

After the optional concentration step, the filtered and/or concentrated plasma is sterilized by any means known in the art. In a preferred embodiment, the plasma is bottled or packaged using standard procedures in the form in which it will be distributed. The packaged plasma is then frozen to a hard freeze condition of a temperature of about −23° C. (−10° F.). While still frozen, the packaged plasma is then subjected to sufficient gamma irradiation so as to sterilize the plasma without denaturing the immunoglobulin and other immune protein constituents. The level of radiation required for these purposes may vary for each different species from which the plasma is obtained, but may be determined by those skilled in the art without undue experimentation. In the case of equine serum, it is recommended to irradiate the plasma to levels ranging from 3.0 to 5.0 Mrad.

It is important to maintain the packaged plasma in a sufficiently hard frozen state during the irradiation step in order to avoid denaturing. For this reason, the plasma is frozen to a relatively low temperature. If it is found that the irradiation process is sufficiently short, or refrigeration is provided during irradiation, then a higher temperature (though still below freezing) may be tolerated. Once the step of sterilizing the serum is completed, the frozen plasma may be thawed and stored at refrigeration temperatures ranging from 2 to 7° C.

The improved plasma may be used in any manner now or later developed for Ig compositions including the novel methods disclosed in this application and/or disclosed in U.S. Ser. No. 08/349,010, incorporated herein by reference. Of particular import, the Ig composition of the present invention may be used to boost the immune system of animals including humans and livestock or domesticated animals including cattle, horses, goats, chickens, pigs, dogs, and cats. The Ig composition may be used to provide passive immunity to infants suffering from hypogammaglobulinemia and/or failure of passive transfer. The Ig composition may also be used alone or in conjunction with conventional antibiotic therapy in treating bacterial or viral infections, and may be used in treating auto-immune diseases.

In the case of cattle, the best mode known for boosting the immune system or treating failure of passive transfer is to orally administer a concentrated Ig composition prepared from bovine whole blood by the inventive method disclosed herein within the first twelve hours of life. If later administered, the Ig composition should be provided intravenously. In this embodiment, the Ig composition will preferably have an IgG concentration ranging from 1 to 7 g/100 ml of the composition is preferably administered in doses ranging from 250 to 300 ml.

In the case of neonatal goats, it is preferred that a concentrated Ig composition obtained from caprine whole blood in accordance with the inventive method disclosed herein be orally administered to the goats. Preferably, the Ig composition will have an IgG concentration of 1 to 7 g/100 ml of the composition and is administered in amounts ranging from 0.5 to 3.0 g/kg body weight of the goat.

With respect to neonatal swine, the best mode known of boosting the immune system of the swine and treating failure of passive transfer is to administer a concentrated Ig composition obtained from porcine whole blood in accordance with the inventive method disclosed herein. Preferably, the Ig composition will have an IgG concentration ranging from 1 to 7 g/100 ml of the composition and is administered orally in amounts ranging from 0.5 to 3.0 g/kg body weight of the animal. Most preferably, the Ig composition will be administered within the first twenty-four hours of life.

With respect to horses, it is recommended that a concentrated Ig composition obtained from equine whole blood in accordance with the inventive method disclosed herein be orally administered to the horse within the first 12 hours of life. Preferably, the Ig composition will have an IgG concentration ranging from 1 to 7 g/100 ml of the composition and will be administered in dosage amounts of about 300 ml.

From the foregoing, it will be seen that this invention is one well adapted to obtain all ends and objects hereinabove set forth together with the other advantages which are obvious and inherent. It will be understood that certain features and sub combinations of utility may be employed without reference to other features and subcombinations. This is contemplated by and is within the scope of the claims. Of particular import, it is noted that while the Ig composition obtained by the novel method disclosed in this application is believed to have many advantages over prior Ig compositions, the novel methods of treating various maladies and of enhancing weight gain in animals including humans and livestock animals are not limited to use of the novel Ig composition but may utilize any Ig composition as that term is defined herein. Furthermore, the novel methods of administering Ig compositions such as of direct application to the area of infection, subcutaneous injection, intratracheal injection and vapor inhalation may be applicable to treating other maladies not specifically referred to herein.

Since many possible embodiments may be made of the invention without departing from the scope thereof, it is to be understood that all matters herein set forth is to be interpreted as illustrated and not in a limiting sense.

What is claimed is:

1. A method of treating a stress induced respiratory disorder in a horse, wherein said method comprises administering to said horse a therapeutically effective amount of an immunoglobulin composition comprising equine IgG and wherein said stress induced respiratory disorder is exercise induced pulmonary hemorrhage.

2. A method in accordance with claim 1, wherein said immunoglobulin composition is administered three to five times within a period ranging from six to ten days.

3. A method in accordance with claim 1, wherein said immnunoglobulin composition is administered every seven to ten days.

4. A method in accordance with claim 1, wherein said immunoglobulin composition is administered in doses ranging from 5 to 20 ml of said immunoglobulin composition.

5. A method in accordance with claim 1, wherein said immunoglobulin composition is administered by a mode selected from the group consisting of intratracheal administration, vapor inhalation, intravenous administration, and/or combinations thereof.

6. A method in accordance with claim 5, wherein said immunoglobulin composition is administered by intratracheal injection and intravenous injection.

7. A method in accordance with claim 5, wherein said immunoglobulin composition is administered by vapor inhalation.

8. A method in accordance with claim 5, wherein said immunoglobulin composition is administered by intratracheal injection.

9. A method in accordance with claim 7, wherein said immunoglobulin composition is administered three to live times within a period ranging from six to ten days.

10. A method in accordance with claim 7, wherein said immunoglobulin composition is administered every seven to ten days.

11. A method in accordance with claim 7, wherein said immunoglobulin composition is administered in doses ranging from 5 to 20 ml of said immunoglobulin composition.

12. A method in accordance with claim 1, wherein said immunoglobulin composition additionally comprises a concentrated amount of one or more gamma globulins selected from the group consisting of IgM, IgA, IgE, IgD and/or mixtures thereof.

13. A method according to claim 1, wherein said immunoglobulin composition comprises IgG immunoglobulins specific to a variety of different antigens.

14. A method according to claim 13, wherein said immunoglobulin composition additionally comprises complement.

* * * * *

UNITED STATES PATENT AND TRADEMARK OFFICE
CERTIFICATE OF CORRECTION

PATENT NO. : 6,770,278 B1 Page 1 of 1
DATED : August 3, 2004
INVENTOR(S) : William G. Skelly It is certified that error appears in the above-identified patent and that said Letters Patent is hereby corrected as shown below:

Column 2,
Line 48, delete "ova" and insert -- over -- therefor.

Column 12,
Line 12, delete "live" and insert -- five -- therefor.

Signed and Sealed this

Twenty-third Day of November, 2004

JON W. DUDAS
*Director of the United States Patent and Trademark Office*